US012389902B2

United States Patent
Quintini et al.

(10) Patent No.: US 12,389,902 B2
(45) Date of Patent: Aug. 19, 2025

(54) DEVICE FOR SUPPORT OF AN ORGAN EX VIVO AND METHOD USING SUCH DEVICE

(71) Applicant: THE CLEVELAND CLINIC FOUNDATION, Cleveland, OH (US)

(72) Inventors: Cristiano Quintini, Cleveland, OH (US); John W. Etterling, Cleveland, OH (US); Daniele Pezzati, Cleveland, OH (US); Qiang Liu, Cleveland, OH (US); Ahmed Hassan, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 673 days.

(21) Appl. No.: 17/846,224

(22) Filed: Jun. 22, 2022

(65) Prior Publication Data

US 2022/0312759 A1 Oct. 6, 2022

Related U.S. Application Data

(62) Division of application No. 16/131,210, filed on Sep. 14, 2018, now Pat. No. 11,399,536.

(Continued)

(51) Int. Cl.
*A01N 1/142* (2025.01)
*A01N 1/10* (2025.01)
(Continued)

(52) U.S. Cl.
CPC ............... *A01N 1/142* (2025.01); *A01N 1/10* (2025.01); *A01N 1/143* (2025.01); *A01N 1/146* (2025.01); *A61B 2017/00969* (2013.01)

(58) Field of Classification Search
CPC .......... A01N 1/10; A01N 1/143; A01N 1/146; A01N 1/142; A01N 1/14; A01N 1/00; A61M 1/0272; A61M 1/0277; C12N 5/54
See application file for complete search history.

(56) References Cited

U.S. PATENT DOCUMENTS

| 7,749,693 B2 | 7/2010 | Brassil et al. |
| 8,507,263 B2 | 8/2013 | Asnaghi et al. |

(Continued)

FOREIGN PATENT DOCUMENTS

| CN | 103800160 A | 5/2014 |
| WO | 96/30111 A1 | 10/1996 |
| WO | 97/49370 A1 | 12/1997 |

OTHER PUBLICATIONS

PCT International Search Report and Written opinion for International Application Serial No. PCT/US2018/051020, mailed Dec. 13, 2018, pp. 1-15.

*Primary Examiner* — Elizabeth A Robinson
*Assistant Examiner* — Tingchen Shi
(74) *Attorney, Agent, or Firm* — Tarolli, Sundheim, Covell & Tummino LLP

(57) ABSTRACT

A device for support of an organ ex vivo comprises a chamber with a first engagement feature. A support structure includes a second engagement feature. The first and second engagement features may be engaged so that the chamber body is carried by the support structure for rotation. The chamber body comprises first and second chamber components. In a first orientation of the chamber body, the first chamber component provides support for a first surface of the organ, and the second chamber component is removable so that a second surface of the organ is exposed to manipulation from outside the chamber body. In a second orientation of the chamber body, the second chamber component provides support for the second surface of the organ, and the first chamber component is removable so that the first surface of the organ is exposed to manipulation from outside the chamber body.

20 Claims, 6 Drawing Sheets

Related U.S. Application Data

(60) Provisional application No. 62/619,271, filed on Jan. 19, 2018, provisional application No. 62/559,198, filed on Sep. 15, 2017.

(51) Int. Cl.
*A01N 1/143* (2025.01)
*A01N 1/146* (2025.01)
*A61B 17/00* (2006.01)

(56) References Cited

U.S. PATENT DOCUMENTS

| | | | |
|---|---|---|---|
| 9,119,392 B2 | 9/2015 | Faulkner et al. | |
| 2003/0168370 A1* | 9/2003 | Merboth | A61F 2/0095 206/438 |
| 2007/0275363 A1* | 11/2007 | Bertram | A01N 1/143 435/297.3 |
| 2012/0116152 A1 | 5/2012 | Faulkner et al. | |
| 2014/0272922 A1 | 9/2014 | Olson et al. | |

\* cited by examiner

DEVICE FOR SUPPORT OF AN ORGAN EX VIVO AND METHOD USING SUCH DEVICE

RELATED APPLICATION

This application is a divisional of U.S. patent application Ser. No. 16/131,210, filed Sep. 14, 2018, which claims priority to U.S. Provisional Patent Application Ser. No. 62/559,198, filed Sep. 15, 2017, and to U.S. Provisional Patent Application Ser. No. 62/619,271, filed Jan. 19, 2018, the subject matter of each of which is incorporated herein by reference in its entirety.

FIELD OF THE INVENTION

The present invention relates to a device for support of an organ or tissue ex vivo and to a method using such a device and, more particularly, to a device that comprises both a chamber with removable components and structure carrying the chamber for rotation into first and second orientations and to a method that uses such a device.

BACKGROUND OF THE INVENTION

In the transplantation of organs, it may be desired to perform a medical procedure on the organ ex vivo before implantation into a patient. A surgeon may, for example, remove excess or damaged tissue from the organ before implantation into the patient. In the case of a liver, the surgeon may divide the liver so that the divided sections of the liver may be implanted into different patients. The more an organ is handled or manipulated ex vivo, however, the greater the likelihood of damage to the organ as a result of such handling. It is desirable, therefore, to reduce the amount of handling of an organ ex vivo, while still permitting the surgeon to perform necessary or desired procedures on the organ prior to implantation.

SUMMARY OF THE INVENTION

The present invention is directed to a device for support of an organ or tissue ex vivo and to a method using such a device and, more particularly, to a device that comprises both a chamber with removable components and structure carrying the chamber for rotation into first and second orientations and to a method that uses such a device.

In accordance with an embodiment of the present invention, a device for support of an organ or tissue ex vivo comprises a chamber that includes a chamber body configured and dimensioned to extend around the organ or tissue ex vivo. The chamber includes a first engagement feature. The device also comprises a support structure that includes a second engagement feature. The second engagement feature is configured and dimensioned to engage the first engagement feature such that the chamber body is carried by the support structure for rotation about an axis extending through the chamber from a first side of the chamber to an opposite second side of the chamber. The chamber body comprises a first removable chamber component and a second removable chamber component. The chamber body when carried by the support structure is rotatable around the axis from a first orientation to a second orientation. The second orientation is different than the first orientation. The first removable chamber component in the first orientation of the chamber body provides support for a first surface of the organ or tissue ex vivo when disposed in the chamber body. The second removable chamber component in the second orientation of the chamber body provides support for a second surface of the organ or tissue ex vivo when disposed in the chamber body. The second removable chamber component is removable from engagement with the chamber body without disengaging the first and second engagement features from one another when the organ or tissue is disposed in the chamber body and the chamber body is in the first orientation so that the first removable chamber component provides support for the first surface of the organ or tissue while the second surface of the organ or tissue is exposed to manipulation from outside the chamber body. The first removable chamber component is removable from engagement with the chamber body without disengaging the first and second engagement features from one another when the organ or tissue is disposed in the chamber body and the chamber body is in the second orientation so that the second removable chamber component provides support for the second surface of the organ or tissue while the first surface of the organ or tissue is exposed to manipulation from outside the chamber body.

In accordance with another embodiment of the invention, a method for performing a surgical procedure uses a device comprising a chamber including a chamber body configured and dimensioned to extend around an organ or tissue ex vivo. The chamber body includes a first removable chamber component and a second removable chamber component. The chamber also includes a first engagement feature. The device also comprises support structure including a second engagement feature configured and dimensioned to engage the first engagement feature such that the chamber body is carried by the support structure for rotation about an axis extending through the chamber from a first side of the chamber to an opposite second side of the chamber. The method comprising the step of positioning the chamber body including the first removable chamber component such that the support structure carries the chamber body and the chamber body is in a first orientation. The method also comprises the step of disposing an ex vivo organ or tissue in the chamber body so that a first surface of the ex vivo organ or tissue is supported by the first removable chamber component and a second surface of the ex vivo organ or tissue is exposed to manipulation from outside the chamber body. The method further comprises the steps of performing a first surgical procedure on the ex vivo organ or tissue, engaging the second removable chamber component with the chamber body, and rotating the chamber body including the first and second removable chamber components around the axis from the first orientation to a second orientation. Further still, the method comprises the step removing the first removable chamber component from engagement with the chamber body so that the second surface of the ex vivo organ or tissue is supported by the second removable chamber component and the first surface of the ex vivo organ or tissue is exposed to manipulation from outside the chamber body. The method yet still further comprises the step of performing a second surgical procedure on the ex vivo organ or tissue.

BRIEF DESCRIPTION OF THE DRAWINGS

The foregoing and other features and advantages of the present invention will become apparent to one skilled in the art upon consideration of the following description of the invention and the accompanying drawings, in which.

DETAILED DESCRIPTION

FIGS. 1 through 6 illustrate a device 10 for support of an organ or tissue ex vivo, in accordance with an example of the present invention. The device 10 includes a chamber 12, support structure 14, and a basin 16.

Figure 4:
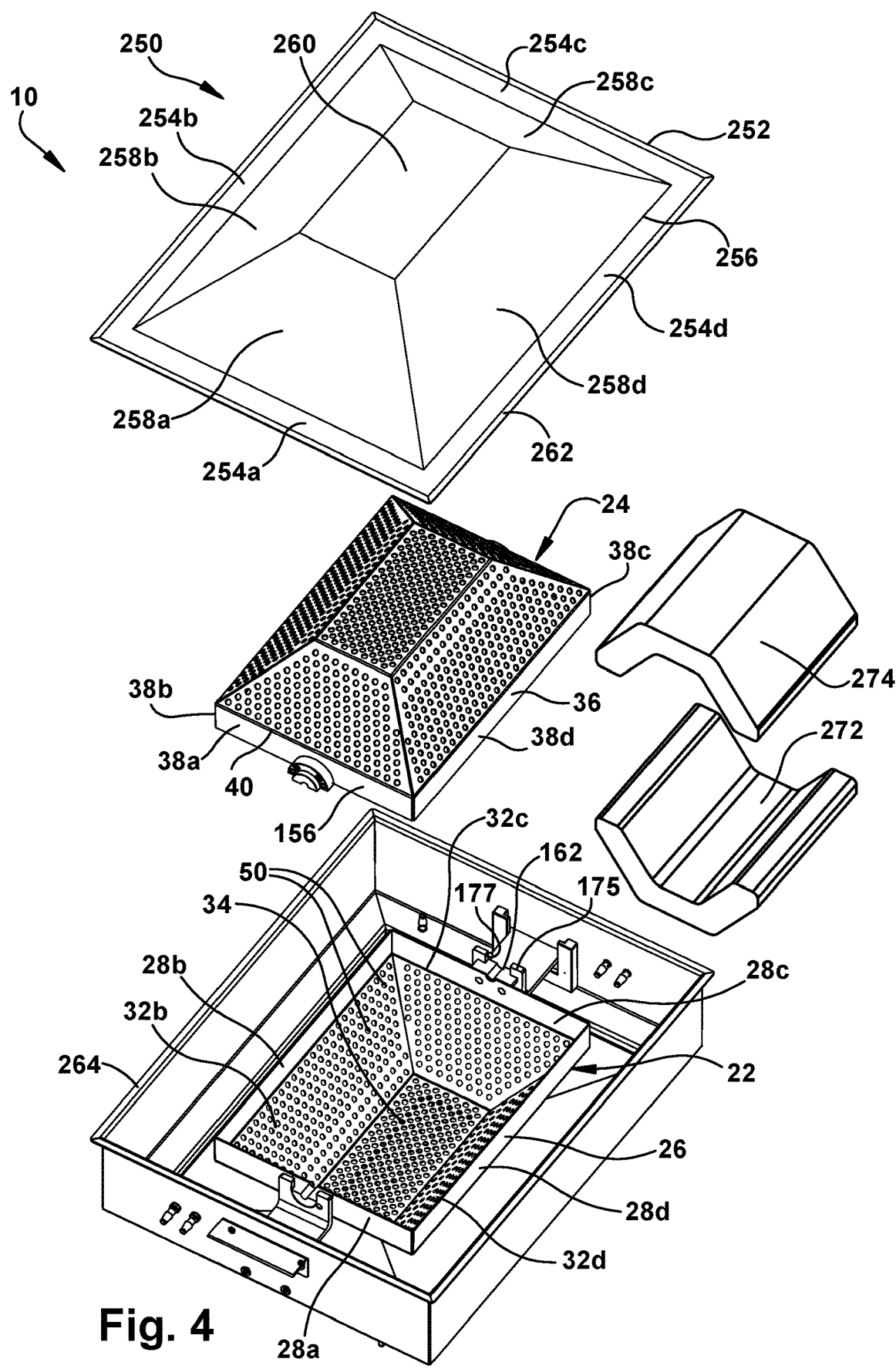
FIG. 4 is an exploded view of the device of FIG. 1

The chamber 12 includes a chamber body 18 and a first engagement feature or chamber-mounted engagement feature 20 attached directly to or connected directly to the chamber body. The chamber body 18 includes a removable first chamber half or first chamber component 22 and a removable second chamber half or second chamber component 24. As best seen in FIG. 4, the first and second chamber components 22 and 24 are substantially identical in configuration and dimensions, including being substantially identical in both size and shape.

Each of the first and second chamber components 22 and 24 is shaped generally like a frustum of a pyramid. Specifically, the first chamber component 22 includes a rectangular rim 26 with four orthogonally disposed legs or sides 28a, 28b, 28c, and 28d. Two opposed sides 28b and 28d are longer than the remaining two sides 28a and 28c so that the rim 26 has a rectangular shape when viewed from above. Extending downward, as viewed in FIGS. 1 and 4, from a lower edge 30 of the rim 26 along the four sides 28a, 28b, 28c, and 28d are four angled side members 32a, 32b, 32c, and 32d that are joined together in the shape of a frustum of a hollow pyramid. Along their respective lower edges, the four angled side members 32a, 32b, 32c, and 32d are joined to a flat base member 34.

In a similar manner, the second chamber component 24 includes a rectangular rim 36 with four orthogonally disposed legs or sides 38a, 38b, 38c, and 38d. Two opposed sides 38b and 38d are longer than the remaining two sides 38a and 38c so that the rim 36 has a rectangular shape when viewed from above. Extending upward, as viewed in FIGS. 1 and 4, from an upper edge 40 of the rim 36 along the four sides 38a, 38b, 38c, and 38d are four angled side members 42a, 42b, 42c, and 42d that are joined together in the shape of a frustum of a hollow pyramid. Along their respective upper edges, the four angled side members 42a, 42b, 42c, and 42d are joined to a flat base member 44.

Figure 1:
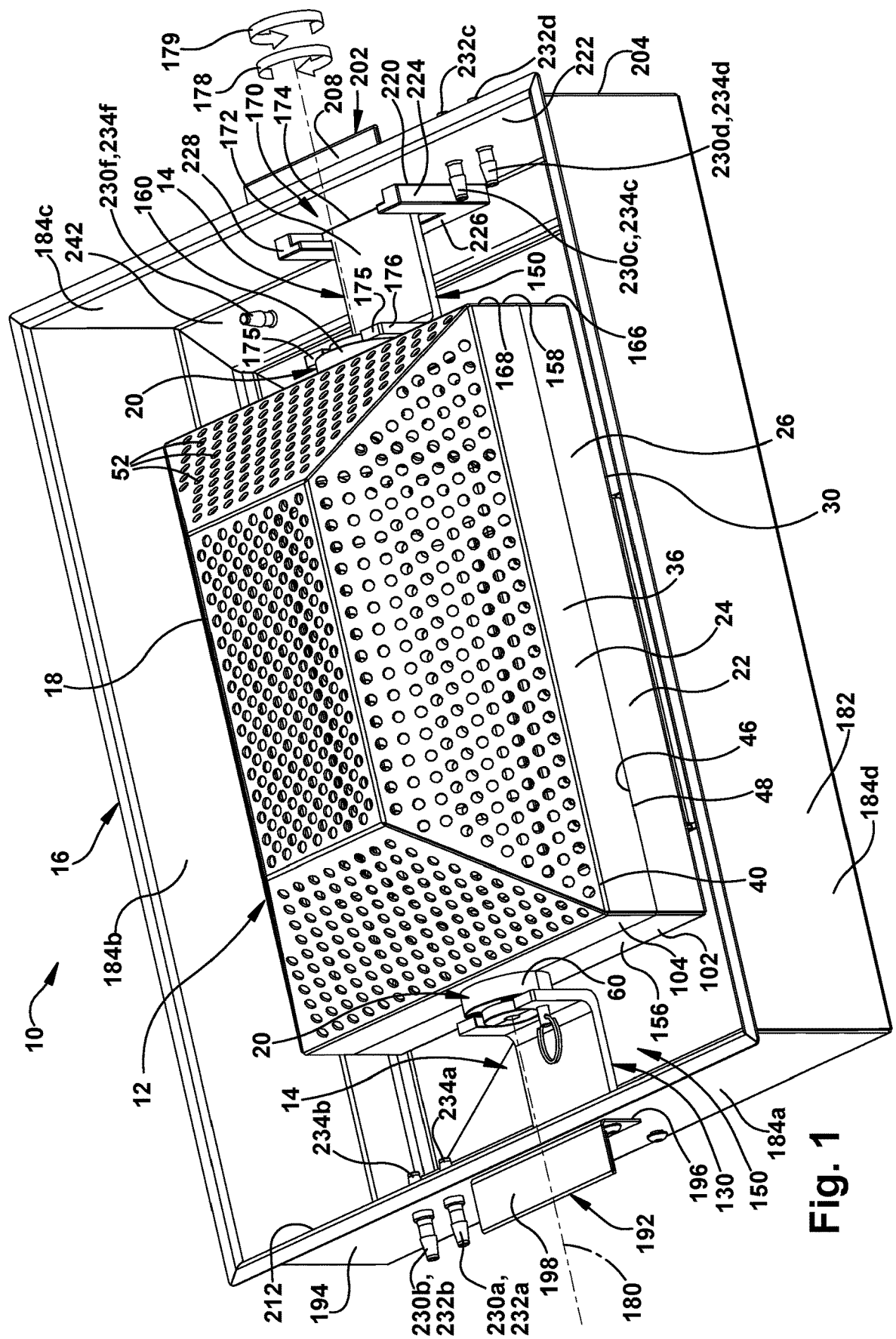
FIG. 1 is a perspective view of an assembled device for support of an organ or tissue ex vivo in accordance with the present invention.
Figure 2:
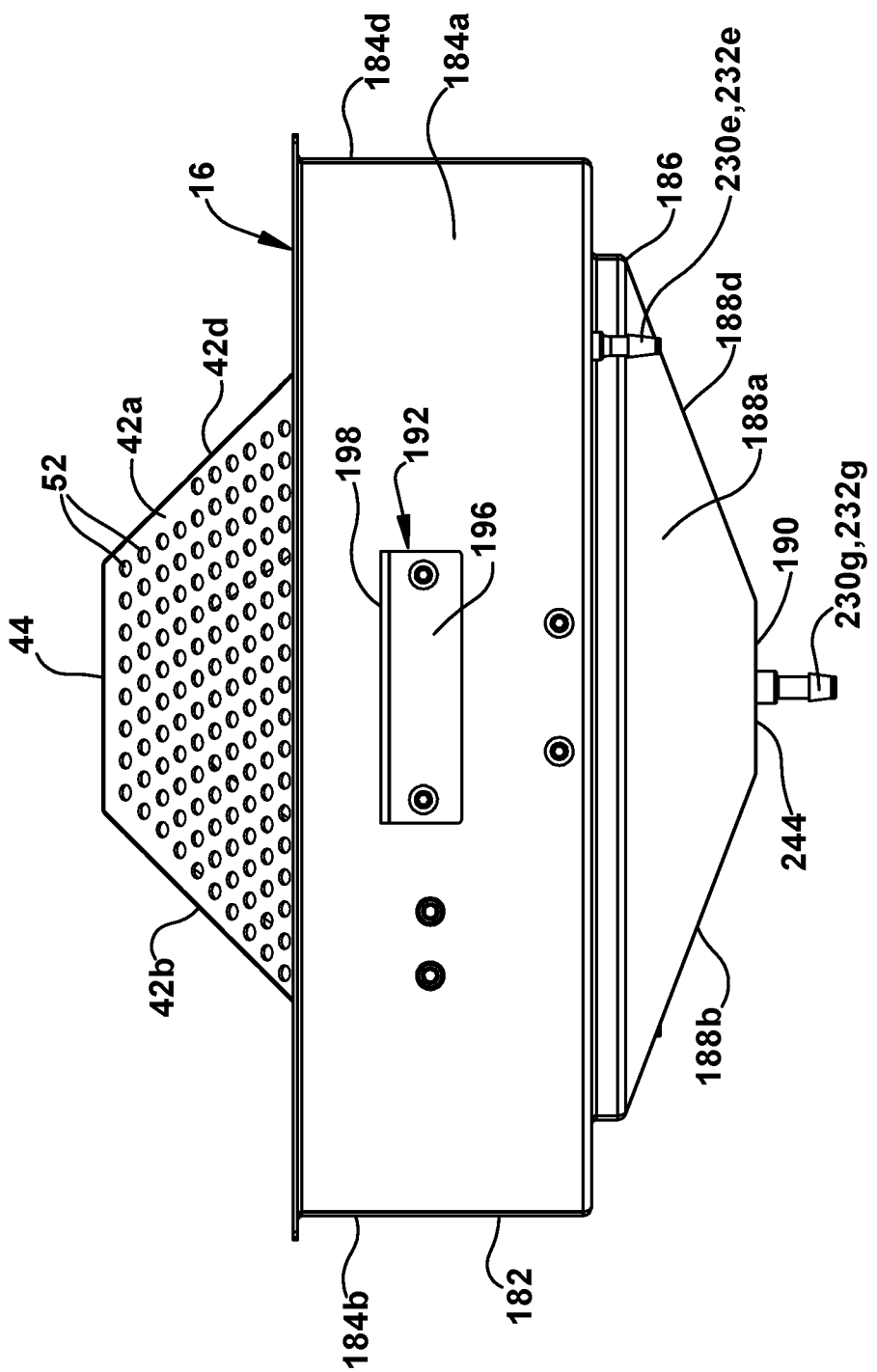
FIG. 2 is an side view of the device of FIG. 1.
Figure 3:
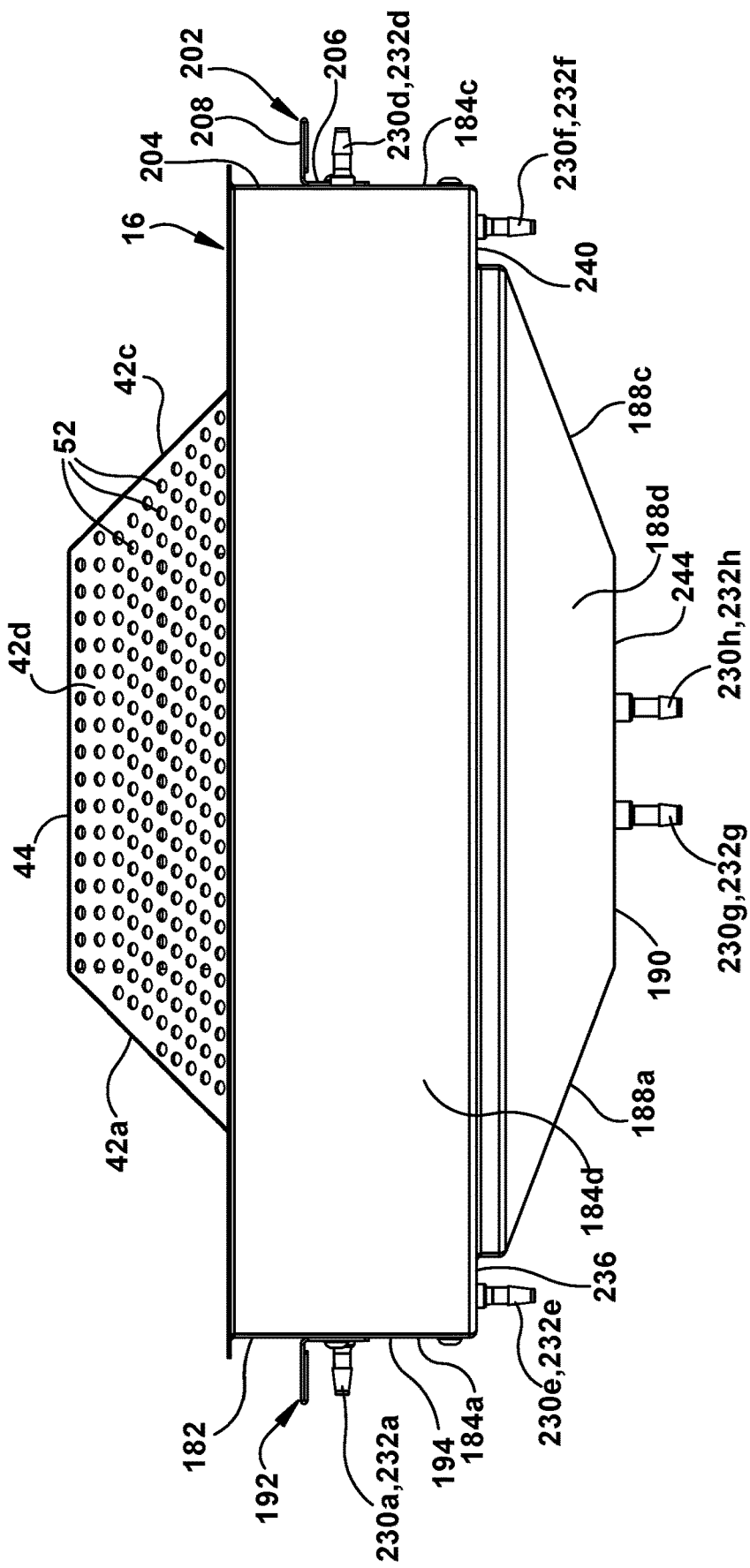
FIG. 3 is a side view of the device of FIG. 1 orthogonal to the view of FIG. 2.

As may be apparent from FIG. 1, an upper edge 46 of the rim 26 of the first chamber component 22 and a lower edge 48 of the rim 36 of the second chamber component 24 are configured and dimensioned to mate with one another. Both the upper edge 46 of the rim 26 and the lower edge 48 of the rim 36 may be flat, as shown. Alternatively, the upper edge 46 of the rim 26 and the lower edge 48 of the rim 36 may include inter-engageable mating features, such as laterally offset raised ridges or lips (not shown). The position of such a lip on the upper edge 46 of the rim 26 may be complementary to the position of such a lip on the lower edge 48 of the rim 36 to help keep the first and second chamber components 22 and 24 from sliding or otherwise moving laterally or side-to-side (as viewed in FIGS. 1 and 4) relative to one another. For example, such a lip on the upper edge 46 of the rim 26 may be dimensioned to lie outside of and extend around the complementary lip on the lower edge 48 of the rim 36 when the first and second chamber components 22 and 24 are positioned in engagement with one another.

The first and second chamber components 22 and 24 may be formed of metal, plastic, or any other relatively rigid material. The rigidity of the material of which the first and second chamber components 22 and 24 is formed may be sufficient to support the weight of an organ or tissue ex vivo without deflection and also sufficient to support or resist without deflection any pressure applied during a medical or surgical procedure on the organ or tissue supported ex vivo on the first and/or second chamber component. Particularly if the first and second chamber components 22 and 24 are formed of plastic, the first and second chamber components may be single use disposable members. Alternatively, and particularly if the first and second chamber components 22 and 24 are formed of metal, the first and second chamber components may be sterilizable re-usable members.

As can be seen in FIGS. 1 and 4, the first and second chamber components 22 and 24 include one or more drainage holes, passages, or openings 50 and 52, respectively, which extend from inside the first and second chamber components to outside the first and second chamber components so as to facilitate drainage of fluids, such as blood and other liquids, from the first and second chamber components. One or more openings 50 and 52 may extend through the base members 34 and 44 from inside the respective first or second chamber component 22 or 24 to outside the respective first or second chamber component. One or more openings 50 and 52 may also or alternatively extend through one or more of the four angled side members 32a, 32b, 32c, and 32d of the first chamber component 22 and/or one or more of the four angled side members 42a, 42b, 42c, and 42d of the second chamber component 24 from inside the respective first or second chamber component to outside the respective first or second chamber component. To provide the openings 50 and 52, the base members 34 and 44 and/or the angled side members 32a, 32b, 32c, 32d and 42a, 42b, 42c, 42d may, for example, be formed of mesh material or of perforated sheet material.

Attached to or mounted to or on the chamber body 18, as previously indicated, is the chamber-mounted engagement feature 20. The chamber-mounted engagement feature 20 comprises a stepped first cylinder, stepped first circular member, or stepped first disc 60, which is directly attached to or directly connected to a first side of the chamber body 18, and a stepped second cylinder, stepped second circular member, or stepped second disc 160, which is directly attached to or directly connected to an opposite second side of the chamber body. The first and second discs 60 and 160 are substantially the same in configuration and size. Accordingly, while only the first disc 60 is described in detail, the second disc 160 includes all of the structure and features that are found in the first disc.

Figure 5:
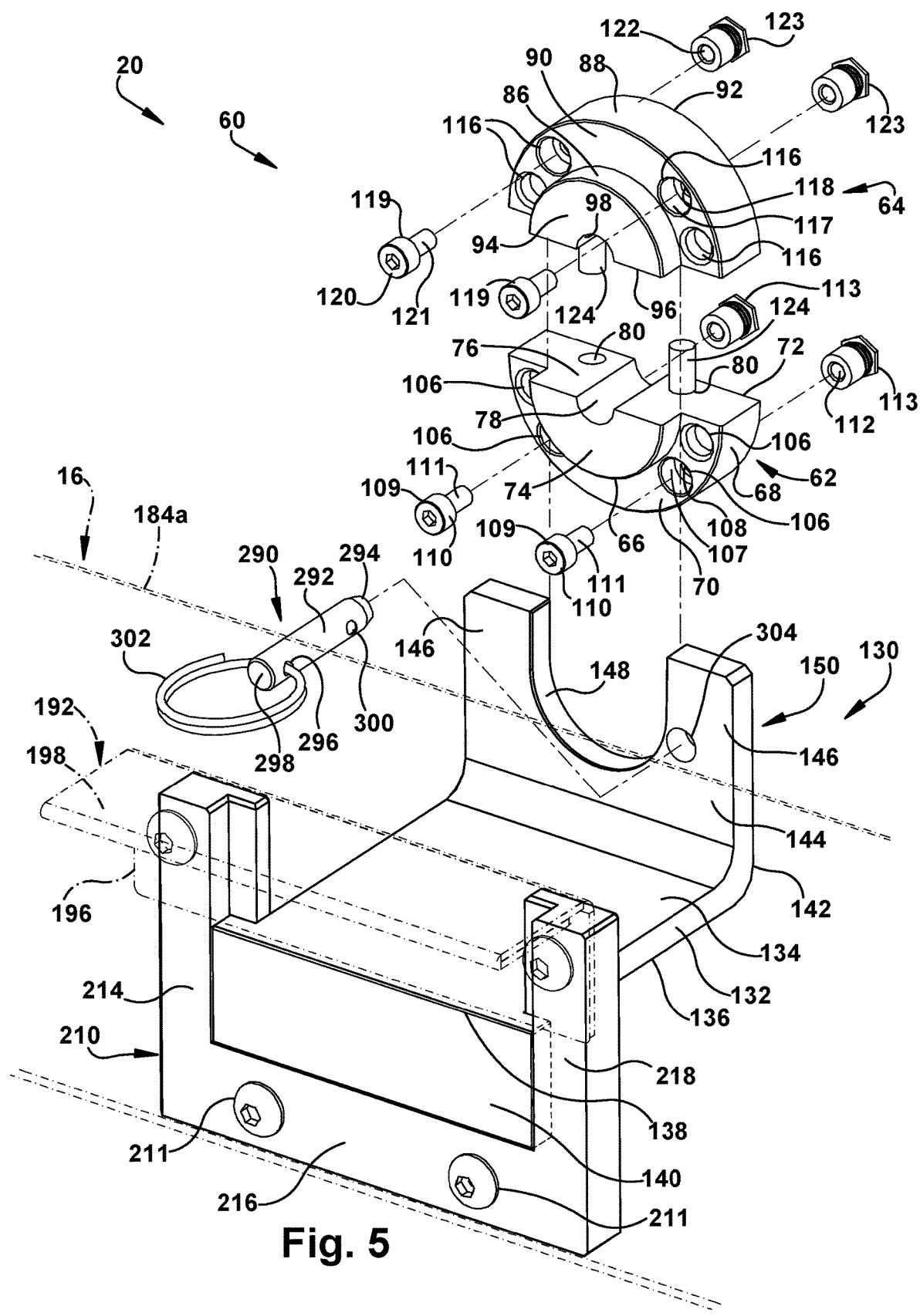
FIG. 5 is an exploded view of certain components of the device of FIG. 1.

The first cylinder or first disc 60 is formed as two inter-engageable cylinder or disc halves or portions 62 and 64. As best seen in FIG. 5, first disc portion 62 has a smaller diameter semi-cylindrical outer surface 66 and a larger diameter semi-cylindrical outer surface 68. Extending between and joining the semi-cylindrical outer surfaces 66 and 68 is a flat semi-annular outer surface 70. Spaced apart or separated from the flat semi-annular outer surface 70 by the larger diameter semi-cylindrical outer surface 68 is a flat semi-circular end surface 72, which extends parallel to the semi-annular outer surface 70. Spaced apart or separated from the flat semi-annular outer surface 70 by the smaller diameter semi-cylindrical outer surface 66 is a flat semi-circular end surface 74, which extends parallel to the semi-annular outer surface 70 and to the end surface 72. Extending from the end surface 72 to the end surface 74 along a plane that includes diameters of the semi-cylindrical outer surfaces 66 and 68 is a flat T-shaped mating surface 76. The T-shaped mating surface 76 mates with a corresponding surface of the second disc portion 64. Also extending from the end surface 72 to the end surface 74 is a concave semi-cylindrical surface 78, which extends along, but is narrower than, the "vertical" or "upright portion" of the "T" of the mating surface 76. Adjacent the end surface 72, two cylindrical openings or recesses 80 are formed in the mating surface 76, with one recess being positioned on each side of the concave semi-cylindrical surface 78.

Like the first disc portion 62, second disc portion 64 has a smaller diameter semi-cylindrical outer surface 86 and a larger diameter semi-cylindrical outer surface 88. Extending between and joining the semi-cylindrical outer surfaces 86 and 88 is a flat semi-annular outer surface 90. Spaced apart or separated from the flat semi-annular outer surface 90 by the larger diameter semi-cylindrical outer surface 88 is a flat semi-circular end surface 92, which extends parallel to the semi-annular outer surface 90. Spaced apart or separated from the flat semi-annular outer surface 90 by the smaller diameter semi-cylindrical outer surface 86 is a flat semicircular end surface 94, which extends parallel to the semi-annular outer surface 90 and to the end surface 92. Extending from the end surface 92 to the end surface 94 along a plane that includes diameters of the semi-cylindrical outer surfaces 86 and 88 is a flat T-shaped mating surface 96. The T-shaped mating surface 96 mates with the mating surface 76 of the first disc portion 62, as will be explained in more detail below. Also extending from the end surface 92 to the end surface 94 is a concave semi-cylindrical surface 98, which extends along, but is narrower than, the "vertical" or "upright portion" of the T-shaped mating surface 96. Adjacent the end surface 92, two cylindrical openings or recesses (not shown) are formed in the mating surface 96, with one recess being positioned on each side of the concave semi-cylindrical surface 98.

Each of the first and second disc portions 62 and 64 of the chamber-mounted engagement feature 20 is directly attached to a corresponding first or second chamber component 22 or 24. More particularly, the first disc portion 62 of the first disc 60 of the chamber-mounted engagement feature 20 is directly attached to or directly connected to a first side 102 of the first chamber component 22. The second disc portion 64 of the first disc 60 of the chamber-mounted engagement feature 20 is directly attached to or directly connected to a first side 104 of the second chamber component 24.

To attach the first disc portion 62 to the first chamber component 22, four recesses or passages 106 are formed in the first disc portion. The passages 106 extend from the flat semi-annular outer surface 70 of the first disc portion 62 to the flat end surface 72. Two of the passages 106 are stepped. The larger diameter portion 107 of each such stepped passage 106 is located adjacent the flat semi-annular outer surface 70 and the smaller diameter portion 108 of each such stepped passage 106 is located adjacent the end surface 72. Threaded fasteners 109 are inserted into the two stepped passages 106. An enlarged head 110 of each threaded fastener 109 engages the step formed in the corresponding stepped passage 106, and a threaded shank 111 of the fastener is screwed into a threaded socket 112 of a nut 113 that engages an inwardly facing or inner surface of the side 28a of the rim 26 of the first chamber component 22. In a similar manner, to attach the second disc portion 64 to the second chamber component 24, four recesses or passages 116 are formed in the second disc portion. The passages 116 extend from the flat semi-annular outer surface 90 of the second disc portion 64 to the flat end surface 92. Two of the passages 116 are stepped. The larger diameter portion 117 of each passage 116 is located adjacent the flat semi-annular outer surface 90 and the smaller diameter portion 118 of each passage 116 is located adjacent the end surface 92. Threaded fasteners 119 are inserted into the two stepped passages 116. An enlarged head 120 of each threaded fastener 119 engages the step formed in the corresponding stepped passage 116, and a threaded shank 121 of the fastener is screwed into a threaded socket 122 of a nut 123 that engages an inwardly facing or inner surface of the side 38a of the rim 36 of the second chamber component 24.

The first cylinder or first disc 60 may be formed of metal, plastic, or any other relatively rigid material. Two suitable plastic materials are polytetrafluoroethylene (PTFE), such as a material sold under the brand name Teflon®, and polyoxymethylene, such as a material sold under the brand name Delrin®. The rigidity of the material of which the first disc 60 is formed may be sufficient to support the weight of the chamber 12 and an organ or tissue in the chamber without deflection and also sufficient to support or resist without deflection any pressure applied during a surgical procedure on the organ or tissue in chamber. Depending on the material from which the first disc 60 is made, various alternative mechanisms may be used in lieu of the threaded fasteners for attaching the first disc 60 to the first chamber component 22. For example, if the first disc 60 is formed from metal, it may be possible to weld the first disc to the first chamber component 22. Other alternative attachment mechanisms include adhesives.

To assemble the chamber body 18 and thus the chamber 12, the first and second chamber components 22 and 24 are positioned relative to one another such that the upper edge 46 of the rim 26 of the first chamber component 22 and the lower edge 48 of the rim 36 of the second chamber component 24 mate with one another or are in direct contact or engagement with one another substantially all along their respective perimeters. When the first and second chamber components 22 and 24 are positioned such that the upper edge 46 of the rim 26 of the first chamber component 22 mates with the lower edge 48 of the rim 36 of the second chamber component 24, the flat T-shaped mating surface 76 of the first disc portion 62 and the flat T-shaped mating surface 96 of the second disc portion 64 will be mated with one another or will be positioned in direct contact or engagement with one another throughout substantially all of each surface. To assist in positioning the first and second disc portions 62 and 64 properly with respect to one another and to assist in maintaining the first and second disc portions in proper alignment with one another, dowel pins or indexing pins 124 may be inserted into the recesses 80 formed in the mating surface 76 of the first disc portion 62 and into the recesses (not shown) formed in the mating surface 96 of the second disc portion 64. The recesses 80 in the mating surface 76 of the first disc portion 62 will be aligned with the recesses (not shown) in the mating surface 96 of the second disc portion 64 when the first and second disc portions are properly positioned with respect to one another. Proper positioning of the first and second disc portions 62 and 64 may also assist in properly positioning the first and second chamber components 22 and 24 with respect to one another.

When the chamber body 18 and thus the chamber 12 is assembled with the first and second chamber components 22 and 24 positioned in direct contact or engagement with one another and in alignment with one another, the first and second disc portions 62 and 64 are positioned relative to one such that they form the complete stepped first disc 60, which is a portion of the chamber-mounted engagement feature 20. Because the chamber-mounted engagement feature 20 includes a complete first disc 60, the chamber-mounted engagement feature can facilitate rotation of the chamber body 18 and the chamber 12. In particular, by engaging the chamber-mounted engagement feature 20 with a second engagement feature or support-mounted engagement feature 150 that has a complementary shape and that is incorporated into or mounted to or on the support structure 14, the chamber body 18 and the chamber 12 may be supported or carried by the support structure and also be rotatable about an axis as the chamber-mounted engagement feature is rotated relative to the second engagement feature or support-mounted engagement feature 150. Although such a support-mounted engagement feature 150 and support structure 14 may have numerous different configurations, one particular design of a second engagement feature and support structure is shown generally in FIG. 1 and in detail in FIG. 5.

As generally shown in FIG. 1, the support structure 14 comprises an elongated first bracket 130, which is directly attached to or mounted on a first side of the basin 16, and an elongated second bracket 170, which is directly attached to or mounted on an opposite second side of the basin. The first and second brackets 130 and 170 are substantially the same in configuration and size. Accordingly, while only the first bracket 130 is described in detail, the second bracket 170 includes all of the structure and features that are found in the first bracket.

The first bracket 130 may be formed of metal, plastic, or any other relatively rigid material. The rigidity of the material of which the first bracket 130 is formed may be sufficient to support the weight of the chamber 12 and an organ or tissue in the chamber without deflection and also sufficient to support or resist without deflection any pressure applied during a surgical procedure on the organ or tissue in chamber.

The first bracket 130 includes a rectangular first body portion 132. The first body portion 132 of the first bracket 130 has a first major surface 134, which is substantially rectangular in shape, and an opposite, second major surface 136, which is also substantially rectangular in shape. At one end 138 of the first body portion 132 and thus the first bracket 130, a rectangularly shaped first bracket support portion 140 extends away from the first body portion 132. The first bracket support portion 140 is oriented transverse to and, more particularly, substantially perpendicular to the first body portion 132. The second major surface 136 of the first body portion 132 is presented in substantially the same direction as the first bracket support portion 140 extends. At the opposite end 142 of the first body portion 132 and thus the first bracket 130, a U-shaped first chamber support portion 144 extends away from the first body portion 132. The first chamber support portion 144 is oriented transverse to and, more particularly, substantially perpendicular to the first body portion 132. The first major surface 134 of the first body portion 132 is presented in substantially the same direction as the first chamber support portion 144 extends. The first bracket support portion 140 engages the basin 16 in a manner described in more detail below. The first chamber support portion 144 provides or defines a portion of the support-mounted engagement feature 150, which is configured and dimensioned to engage the chamber-mounted engagement feature 20 such that the chamber body 18 is carried by the support structure 14 for rotation.

As shown in FIG. 5, the first chamber support portion 144 includes two laterally spaced apart projections 146 that form or define the legs of the "U" shape. Extending along the lengths of the two projections 146 and across the first chamber support portion 144 between the two projections is a U-shaped surface 148. The U-shaped surface 148 includes a curved surface portion extending across the first chamber support portion 144 between the two projections 146 and two straight surface portions extending along the lengths of the two projections. The U-shaped surface, including its curved surface portion, is configured and dimensioned to receive each of the smaller diameter semi-cylindrical outer surfaces 66 and 86 of the first and second disc portions 62 and 64, respectively, when the first and second disc portions are engaged with one another to form the first disc 60, when the first disc portion individually or separately engages the U-shaped surface, and when the second disc portion individually or separately engages the U-shaped surface. The first disc 60 is therefore shaped and dimensioned to engage the U-shaped surface 148, including its curved surface portion, throughout approximately one-half of the smaller circumference of the first disc and is free to rotate relative to the U-shaped surface while being supported on the U-shaped surface. Each of the two projections 146 is long enough to extend upwardly beyond the center of the first disc 60 when the first disc 60 is supported by the U-shaped surface 148. The two projections 146 thus tend to keep or maintain the first and second disc portions 62 and 64 from separating or sliding relative to one another as the first disc rotates. The support-mounted engagement feature 150 thus comprises the first chamber support portion 144 of the first bracket 130, including the projections 146 and the U-shaped surface 148, which U-shaped surface includes the curved surface portion.

To engage the chamber-mounted engagement feature 20 with the support-mounted engagement feature 150, the chamber body 18 and the directly attached chamber-mounted engagement feature 20 may be moved vertically in a downward direction, as viewed in FIG. 5, so as to move the first disc 60 between the projections 146 of the first chamber support portion 144 of the first bracket 130 and into contact with the U-shaped surface 148. As a result of such downward movement, the chamber-mounted engagement feature 20 directly engages the support-mounted engagement feature 150. Such movement may be easily accomplished, as can the reverse upward movement required to disengage the chamber body 18 and the chamber-mounted engagement feature 20 from the first chamber support portion 144 of the first bracket 130 and the support-mounted engagement feature 150. Although the U-shape of the first chamber support portion 144 facilitates easy and convenient movement of the chamber-mounted engagement feature 20 into and out of engagement with the support-mounted engagement feature 150, there are numerous alternative configurations for the support-mounted engagement feature 150. For example, one of the projections 146 could be shaped to curve around and over the open end of the "U" shape so that the resulting support-mounted engagement feature 150 would be a substantially circular member with a notch or opening in an upper right or upper left quadrant, as viewed in FIG. 5, of the circular shape through which the first disc 60 could be moved into the substantially circular member and into engagement with the support-mounted engagement feature. As another alternative, the first chamber support portion 144 could simply be formed with a circular bore extending through the first chamber support portion into which the first disc 60 could be moved axially to engage the chamber-mounted engagement feature 20 with the support-mounted engagement feature 150. As a further alternative, the first chamber support portion 144 could include one or more hinged links that could be swung into a position to open a notch or opening through which the first disc 60 could be moved laterally or vertically into engagement with a curved interior support surface 148 of the first chamber support portion.

To this point, the chamber-mounted engagement feature 20 has been described as comprising the stepped first disc 60 directly engaged with or directly attached to the chamber body 18 at a first side 156 of the chamber body and the support-mounted engagement feature 150 has been described as comprising the first chamber support portion 144 of the first bracket 130 located adjacent the stepped first disc 60 and the first side of the chamber body. As previously stated and as shown in FIGS. 1, 4, 5, and 6, the chamber-mounted engagement feature 20 also includes a stepped second cylinder or stepped second disc 160 at a second side 158 of the chamber body 18 opposite the first side 156, and the support-mounted engagement feature 150 also comprises a second chamber support portion 176 of a second bracket 170 located adjacent the stepped second disc 160 and the second side 158 of the chamber body. The stepped second disc 160 is in all respects identical to the stepped first disc 60 and includes two inter-engageable disc halves or disc portions 162 and 164. The first disc portion 162 of the second disc 160 of the chamber-mounted engagement feature 20 is directly attached to or directly connected to a second side 166 of the first chamber component 22 opposite the first side 102. The second disc portion 164 of the second disc 160 of the chamber-mounted engagement feature 20 is directly attached to or directly connected to a second side 168 of the second chamber component 24 opposite the first side 104. Similarly, as previously stated, the second bracket 170 of the support structure 14 is in all respects identical to the first bracket 130 and includes a second body portion 172, a second bracket support portion 174, and a second chamber support portion 176. The support-mounted engagement feature 150 thus also comprises the second chamber support portion 176 of the second bracket 170, including its projections 175 and U-shaped surface 177, which U-shaped surface includes a curved surface portion.

When the first disc 60 is engaged with the first chamber support portion 144 of the first bracket 130 and the second disc 160 is engaged with the second chamber support portion 176 of the second bracket 170, the chamber body 18 and thus the chamber 12 can be rotated about an axis 180 that extends through the chamber from the first side 156 of the chamber to the opposite second side 158 of the chamber. The axis 180 also extends through the centers of the first and second discs 60 and 160. As shown, the chamber body 18 and thus the chamber 12 can be rotated manually via direct engagement by a person's hand in either a clockwise direction 178 around the axis 180 or an opposite counter-clockwise direction 179 around the axis. The chamber body 18 and thus the chamber 12 may also be rotated by a manually operated crank (not shown) that may be connected to one or both of the first and second discs 60 and 160 or by a motor (not shown) that may similarly be connected to one or both of the first and second discs 60 and 160. Such a motor (not shown) may be controlled by a controller (not shown) responsive to inputs from a keyboard (not shown), a touch screen (not shown), and/or one or more sensors (not shown).

As previously described, the first bracket 130 of the support structure 14 is mounted on the basin 16. The second bracket 170 of the support structure 14 is similarly mounted on the basin 16. The basin 16 performs several functions and thus provides several functional features for the device 10. One function is to provide a mounting structure on which the first and second brackets 130 and 170 of the support structure 14 may be mounted. Another function is to provide a container into which fluids, such as blood and other liquids, from an ex vivo organ or tissue in the chamber 12 may drain and/or into which excess, unwanted, or non-viable material from the organ or tissue in the chamber may be placed by a surgeon or other healthcare provider. A further function is to provide a portable carrier to permit or facilitate movement or relocation of the chamber 12 and the support structure 14. The foregoing functions may, however, be provided by other structure or another device or by more than one other structure or other device.

The basin 16 may be formed of metal, plastic, or any other relatively rigid material. The rigidity of the material of which the basin 16 is formed may be sufficient to support the weight of the chamber 12 and an organ or tissue in the chamber without deflection and also sufficient to support or resist without deflection any pressure applied during a surgical procedure on the organ or tissue in chamber. If the basin 16 were not providing a mounting structure on which or to which the first and second brackets 130 and 170 of the support structure 14 are mounted, but were only, for example, providing a container into which fluids from an ex vivo organ or tissue in the chamber 12 may drain and/or into which excess, unwanted, or non-viable material from the organ or tissue in the chamber may be placed by a surgeon or other healthcare provider, the basin may be made from less rigid material As can be seen in FIGS. 1-4, the basin 16 is generally shaped like a frustum of a pyramid and thus is similar in shape to, but with larger dimensions than, the first chamber component 22. The basin 16 includes a rectangular rim 182 with four orthogonally disposed L-shaped legs or sides 184a, 184b, 184c, and 184d. Extending downward, as viewed in FIGS. 2 and 3, from a lower edge 186 of the rim 182 along the inward ends of the four L-shaped sides 184a, 184b, 184c, and 184d are four angled side members 188a, 188b, 188c, and 188d that are joined together in the shape of a frustum of a hollow pyramid. Along their respective lower edges, the four angled side members 188a, 188b, 188c, and 188d are joined to a flat base member 190. Except for certain ports, which will be described hereinafter, all of the rim 182, the four angled side members 188a, 188b, 188c, and 188d, and the flat base member 190 are formed of solid materials free of any openings. The use of solid materials free of openings permits the basin 16 to perform the function of providing a container into which fluids, such as blood and other liquids, from an ex vivo organ or tissue in the chamber 12 may drain and/or into which excess, unwanted, or non-viable material from the organ or tissue in the chamber may be placed by a surgeon or other healthcare provider. The four angled side members 188a, 188b, 188c, and 188d help direct fluids to the base member 190 for collection and disposal. The base member 190 also provides a bottom surface that may facilitate placing the device 10 in a stable position on the top of a medical cart, table, or other structure.

To assist in moving the basin 16 and thus the entire device 10, an L-shaped handle 192 is fixed to or otherwise connected to or attached to an outwardly presented or exterior surface 194 of the side 184a of the rim 182 of the basin 16. One leg 196 of the handle 192 is secured, for example, by welding, by rivets, or by threaded fasteners, such as screws, to the side 184a of the rim 182. The other leg 198 of the handle 192 projects away from the outwardly presented or exterior surface 194 of the side 184a of the rim 182 and may be grasped to help pick up and relocate the basin 16. A similar L-shaped handle 202 is fixed to or otherwise connected to or attached to an outwardly presented or exterior surface 204 of the side 184c of the rim 182 of the basin 16, which is opposite the side 184a to which the handle 192 is fixed or connected or attached. One leg 206 of the handle 202 is secured, for example, by welding, by rivets, or by threaded fasteners, such as screws, to the side 184c of the rim 182. The other leg 208 of the handle 202 projects away from the outwardly presented or exterior surface 204 of the side 184c of the rim 182 and may be grasped to help pick up and relocate the basin 16.

As best seen in FIGS. 1 and 5, to enable the first bracket 130 of the support structure 14 to be removably mounted on the basin 16, a guide 210 is fixed, secured, or otherwise attached, for example, by welding, by rivets, or by threaded fasteners 211, such as screws, to an inwardly presented or interior surface 212 of the side 184a of the rim 182 of the basin 16. The guide 210 includes three linear portions 214, 216, and 218 arranged in the shape of a "U." Each of the linear portions 214, 216, and 218 is L-shaped in cross-section taken orthogonal to its respective length. The guide 210 is fixed to the side 184a of the rim 182 so that a slot is formed between one leg of the L-shape of each linear portion 214, 216, and 218 and the interior surface 212 of the side 184a. The linear portions 214, 216, and 218 of the guide 210 are also fixed or mounted to the side 184a such that the slot formed by each of the upright linear portions 214 and 218 opens toward or is presented toward the slot formed by the opposite linear portion. As a result, the first bracket support portion 140 of the first bracket 130 may be slid, in a downward direction as viewed in FIG. 5, into the oppositely facing slots to mount the first bracket 130 on the basin 16. Movement of the first bracket support portion 140 in a downward direction, as viewed in FIG. 5, is limited by the laterally extending linear portion 216 of the guide 210, which rests on a laterally extending leg of the L-shaped side 184a of the rim 182 of the basin 16.

Similarly, as best seen in FIG. 1, a guide 220 is fixed, secured, or otherwise attached, for example, by welding, by rivets, or by threaded fasteners, such as screws, to an inwardly presented or interior surface 222 of the side 184c of the rim 182 of the basin 16. The guide 220 includes three linear portions 224, 226, and 228 arranged in the shape of a "U." Each of the linear portions 224, 226, and 228 is L-shaped in cross-section taken orthogonal to its respective length. The guide 220 is fixed to the side 184c of the rim 182 so that a slot is formed between one leg of the L-shaped cross-section of each linear portion 224, 226, and 228 and the interior surface 222 of the side 184c. The linear portions 224, 226, and 228 of the guide 220 are also fixed or mounted to the side 184c such that the slot formed by each of the upright linear portions 224 and 228 opens toward or is presented toward the slot formed by the opposite linear portion. As a result, the second bracket support portion 174 of the second bracket 170 may be slid, in a downward direction as viewed in FIG. 1, into the oppositely facing slots to mount the second bracket 170 on the basin 16. Movement of the second bracket support portion 174 in a downward direction, as viewed in FIG. 1, is limited by the laterally extending linear portion 226 of the guide 220, which rests on a laterally extending leg of the L-shaped side 184c of the rim 182 of the basin 16.

To facilitate the delivery of fluids and, more particularly, liquids, to an ex vivo organ or tissue in the chamber 12 and/or to facilitate the insertion of electrical wires into the chamber for connection to sensors in, on or adjacent to an ex vivo organ or tissue in the chamber, multiple ports 230 extend through the rim 182 of the basin 16 and through the base member 190. As shown, two ports 230a and 230b extend through the vertically extending leg of the L-shaped side 184a of the rim 182 from the outwardly presented or exterior surface 194 of the side 184a to the inwardly presented or interior surface 212. Adjacent the exterior surface 194, each of the ports 230a and 230b has an exterior fitting 232a, b to accept and retain a length of plastic tubing. Similarly, adjacent the interior surface 212, each of the ports 230a and 230b has an interior fitting 234a, b to accept and retain a length of plastic tubing. A passage (not shown) extends through each of the ports 230a and 230b so that fluid can flow from an exterior fitting 232 to an interior fitting 234 (or in the opposite direction) or a wire can extend from an exterior fitting to an interior fitting. Likewise, two ports 230c and 230d extend through the vertically extending leg of the L-shaped side 184c of the rim 182 from the outwardly presented or exterior surface 204 of the side 184c to the inwardly presented or interior surface 222. Adjacent the exterior surface 204, each of the ports 230c and 230d has an exterior fitting 232c, d to accept and retain a length of plastic tubing. Similarly, adjacent the interior surface 222, each of the ports 230c and 230d has an interior fitting 234c, d to accept and retain a length of plastic tubing. A passage (not shown) extends through each of the ports 230c and 230d so that fluid can flow from an exterior filling 232c, d to an interior fitting 234c, d (or in the opposite direction) or a wire can extend from an exterior fitting to an interior fitting.

A further port 230e (FIG. 3) extends through the laterally extending leg of the L-shaped side 184a of the rim 182 from an outwardly presented or exterior surface 236 of the side 184a to an opposite inwardly presented or interior surface (not shown). Adjacent the exterior surface 236, the port 230e has an exterior fitting 232e to accept and retain a length of plastic tubing. Similarly, adjacent the interior surface 238, the port 230e has an interior fitting (not shown) to accept and retain a length of plastic tubing. A passage (not shown) extends through the port 230e so that fluid can flow from the exterior fitting 232e to the interior fitting (or in the opposite direction) or a wire can extend from one fitting to the other fitting. Likewise, a port 230f (FIGS. 1 and 3) extends through the laterally extending leg of the L-shaped side 184c of the rim 182 from an outwardly presented or exterior surface 240 of the side 184c to an opposite inwardly presented or interior surface 242. Adjacent the exterior surface 240, the port 230f has an exterior fitting 232f to accept and retain a length of plastic tubing. Similarly, adjacent the interior surface 242, the port 230f has an interior fitting 234f to accept and retain a length of plastic tubing. A passage (not shown) extends through the port 230f so that fluid can flow from the exterior fitting 232f to the interior fitting 234f (in in the opposite direction) or a wire can extend from one fitting to the other fitting.

To assist with drainage of fluids, such as blood and other liquids, from an ex vivo organ or tissue in the chamber 12 and from the basin 16, two ports 230g, h (FIGS. 2 and 3) extend through the base member 190 of the basin 16. As shown, the two ports 230g, h extend through the base member 190 from the outwardly presented or exterior surface 244 of the base to the inwardly presented or interior surface (not shown). Adjacent the exterior surface 244, each of the ports 230g, h has an exterior fitting 232g, h to accept and retain a length of plastic tubing. Adjacent the interior surface (not shown), however, each of the ports 230g, h terminates substantially flush with the interior surface to allow fluids, such as blood and other liquids, directed to the base member 190 to drain into the ports. A passage (not shown) extends through each of the ports 230g, h so that fluid can flow from an interior end of the port to an exterior fitting 232g, h.

The number and locations of the various ports 230 may be varied in accordance with, for example, the intended use of the device 10, the configuration of the chamber 12, and/or the configuration of the basin 16. The device 10 may thus have more or fewer ports 230 than shown and described above, and the ports may be located in different positions, as desired.

As an optional feature to provide a portable carrier to permit or facilitate movement or relocation of the chamber 12 and the support structure 14 and/or to help protect the chamber from the environment, the basin 16 may have a lid 250, as shown in FIG. 4. The lid 250 is generally shaped like a frustum of a pyramid and is similar in shape to the basin 16. The lid 250 includes a rectangular rim 252 with four orthogonally disposed legs or sides 254a, 254b, 254c, and 254d. Extending upward, as viewed in FIG. 4, from an inner edge 256 of the rim 252 along the inward ends of the four sides 254a, 254b, 254c, and 254d are four angled side members 258a, 258b, 258c, and 258d that are joined together in the shape of a frustum of a hollow pyramid. Along their respective upper edges, the four angled side members 258a, 258b, 258c, and 258d are joined to a flat base member 260. All of the rim 252, the four angled side members 258a, 258b, 258c, and 258d, and the flat base member 260 are formed of solid materials free of any openings. An outer edge 262 of the rim 252 extends outwardly and downwardly as a lip and may be supported on a corresponding outwardly and downwardly extending upper edge 264 of the rim 182 of the basin 16 so as to enclose the chamber 12.

Figure 6:
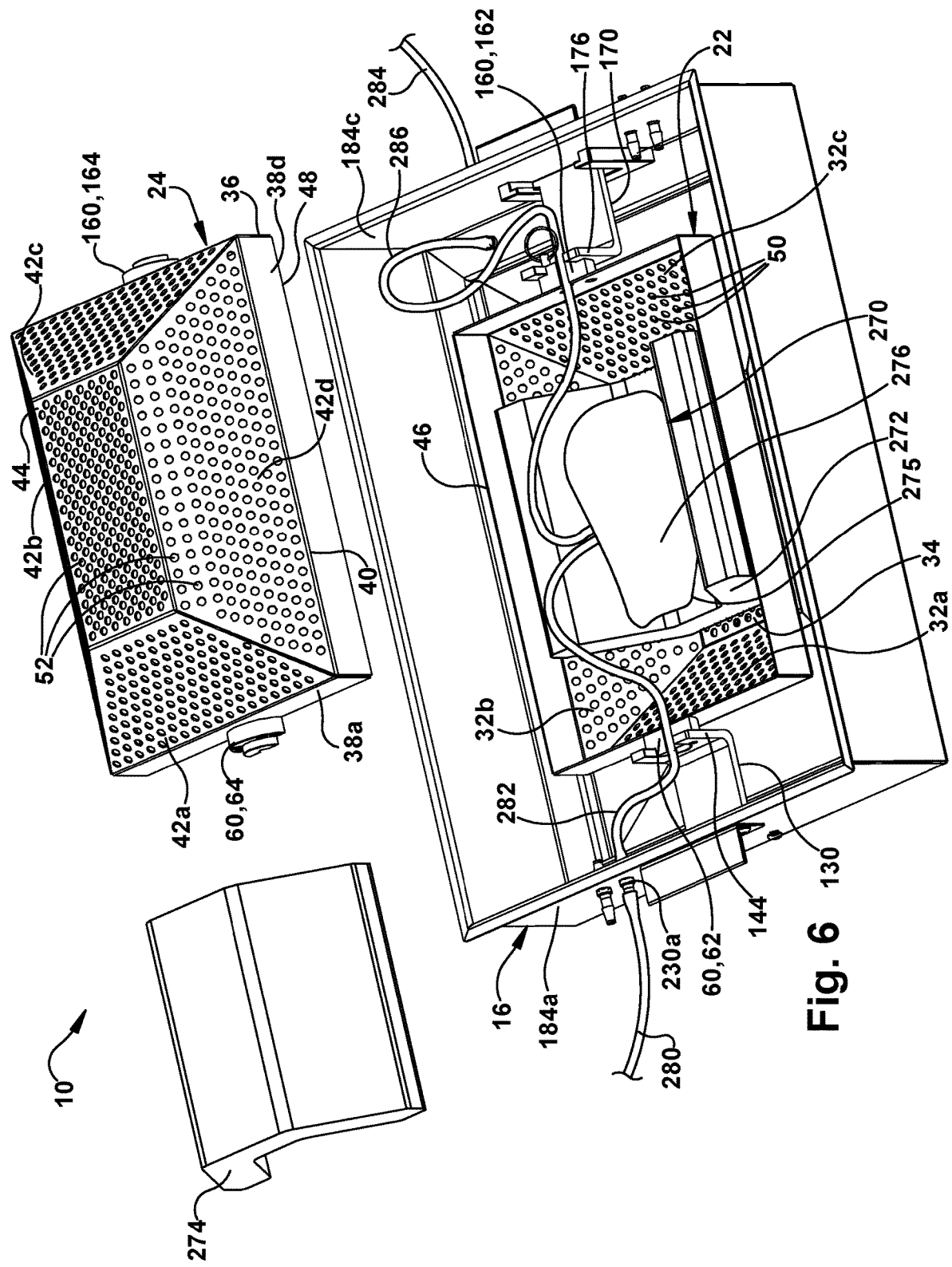
FIG. 6 is a view of the device of FIG. 1 in use.

In preparation for use, the device 10 may be laid out as shown in FIG. 6. In particular, the basin 16 may be supported on a suitable surface or support member (not shown), and the first chamber component 22 may be placed in the basin with the first disc portions 62 and 162 of the first and second discs 60 and 160 in contact with and supported by the first and second chamber support portions 144 and 176 of the first and second brackets 130 and 170. The lid 250 is positioned away from and not in contact with the basin 16 and the second chamber component 24 is similarly portioned away from and not in contact with the first chamber component 22. An ex vivo organ 270, such as a liver, may be placed on a first cushion or first compliant member 272, such as a disposable sponge or foam pad, with a first surface 275 of the organ in contact with the first compliant member. The organ 270 and the first compliant member 272 may then be placed in the first chamber component 22 such that the first compliant member 272 is positioned between the organ and the first chamber component. The first compliant member 272 is sufficiently compliant and shock absorbing to protect the organ 270 from injury from the first chamber component 22 when the chamber is moved. The first compliant member 272 is also sufficiently stiff to permit a medical or surgical procedure to be performed on the organ 270 when supported in the first chamber component 22. The first compliant member 272 is further formed and shaped to allow fluids, such as blood and other liquids, to drain from the organ 270 through the openings 50 in the first chamber component 22 and thus into the basin 16. The first compliant member 272 may optionally include one or more features, such as a glue strip, to help attach the compliant member temporarily and releasably to the first chamber component 22.

To facilitate use of the chamber 12 as intended and as described hereinafter, a second cushion or second compliant member 274 may also be provided. The second compliant member 274 is substantially the same in configuration, dimensions, and construction as the first compliant member 272. The second compliant member 274, when in use, is placed on the organ 270 in contact with a second surface 276 of the organ different than and disposed opposite the first surface 275 of the organ supported by the first compliant member 272. The second chamber component 24 may then be placed on the first chamber component 22 such that the second compliant member 274 is positioned between the organ 270 and the second chamber component. The chamber 12 will then be complete and will surround or be positioned around the organ 270. With the organ 270 disposed between the first and second compliant members 272 and 274 and between the first and second chamber components 22 and 24, the chamber 12 and thus the organ may be rotated about the axis 180 without injury to or significant movement of the organ relative to the chamber.

In the transplantation of organs, such as the organ 270, it is typical to perfuse the organ with a suitable perfusion liquid from at least the point in time at which the organ is harvested or removed from the donor, and potentially prior to removal from the donor, until the point in time at which the organ is placed into the body of a recipient and connected to appropriate vessels and ducts in the recipient's body. To permit perfusion liquid to be delivered to the organ 270, the perfusion liquid must be able to flow from outside the basin 16, through the basin, and into the chamber 12. One arrangement for delivering perfusion liquid to an organ, such as the organ 270, is illustrated in FIG. 6. In FIG. 6, one end of a first length of sterilized, medical grade plastic tubing 280 is connected to a source of perfusion liquid (not shown). The other end of the first length of tubing 280 is connected to the exterior fitting 232a of the port 230a, which extends through the vertically extending leg of the L-shaped side 184a of the rim 182 of the basin 16. One end of a second length of sterilized, medical grade plastic tubing 282 is connected to the interior fitting 234a of the port 230a. The second length of tubing 282 then passes through the first disc 60 from outside the chamber 12 into the interior of the chamber.

To pass through the first disc 60, the second length of tubing 282 extends along the concave semi-cylindrical surface 78 of the first disc portion 62 and/or along the corresponding concave semi-cylindrical surface 98 of the second disc portion 64. When the first chamber component 22 and the second chamber component 24 are in contact with and aligned with one another, the first and second disc portions 62 and 64 will likewise be in contact with and aligned with one another and the concave semi-cylindrical surfaces 78 and 98 will be presented toward each other to define a passage through the first disc 60 into which the second length of tubing 282 may be inserted to pass through the cylinder. The concave semi-cylindrical surfaces 78 and 98 may have a smooth finish, for example, a surface provided by a low friction coating, to allow the first disc 60 to rotate easily without tending to cause the second length of tubing 282 to rotate and thus twist. As an alternative, a short sleeve (not shown) may be inserted into the passage through the first disc 60 or placed around the second length of tubing 282 to facilitate rotation of the first disc relative to the second length of tubing. The end of the second length of tubing 282 inside the chamber 12 may then be connected to the organ 270, for example, to a portal vein or hepatic artery of a liver, for delivery of perfusion liquid to the organ.

For certain organs, such as a liver, it may be desirable or necessary to deliver perfusion liquid to more than one vessel or duct in the organ. If, for example, perfusion liquid is to be delivered at a first pressure and/or flow rate to a first vessel or duct of an organ, such as a portal vein of a liver, and at a second pressure or flow rate to a second vessel or duct or the organ, such a hepatic artery of a liver, it may be desirable or necessary to have a flow of perfusion liquid to the organ separate from the flow through the first and second lengths of tubing 280 and 282. As illustrated in FIG. 6, one end of a third length of sterilized, medical grade plastic tubing 284 is connected to a source of perfusion liquid (not shown). The other end of the third length of tubing 284 is connected to the exterior fitting 232f of the port 230f, which extends through the laterally extending leg of the L-shaped side 184c of the rim 182 of the basin 16. One end of a fourth length of sterilized, medical grade plastic tubing 286 is connected to the interior fitting 234f of the port 230f. The fourth length of tubing 286 then passes through the second disc 160 from outside the chamber 12 into the interior of the chamber.

To pass through the second disc 160, the fourth length of tubing 286 extends along the concave semi-cylindrical surface (not shown) of the first disc portion 162 and/or along the corresponding concave semi-cylindrical surface (not shown) of the second disc portion 164. When the first chamber component 22 and the second chamber component 24 are in contact with and aligned with one another, the first and second disc portions 162 and 164 will likewise be in contact with and aligned with one another and the concave semi-cylindrical surfaces (not shown) will be presented toward each other to define a passage through the second disc 160 into which the fourth length of tubing 286 may be inserted to pass through the cylinder. The concave semi-cylindrical surfaces (not shown) may have a smooth finish, for example, a surface provided by a low friction coating, to allow the second disc 160 to rotate easily without tending to cause the fourth length of tubing 286 to rotate and thus twist. As an alternative, a short sleeve (not shown) may be inserted into the passage through the second disc 160 or placed around the fourth length of tubing 286 to facilitate rotation of the second disc relative to the second length of tubing. The end of the fourth length of tubing 286 inside the chamber 12 may then be connected to the organ 270, for example, to a portal vein or hepatic artery of a liver, for delivery of perfusion liquid to the organ.

Because the chamber-mounted and support-mounted engagement features 20 and 150 are configured and dimensioned to facilitate rotation of the chamber body 18 and thus chamber 12 relative to the support structure 14, it may be necessary to limit, block or prevent such rotation at one or more times during a transplantation surgery to allow a surgeon or other healthcare provider to perform a medical procedure or surgical procedure on the organ 270 in the chamber body. FIG. 5 illustrates one particular mechanism to limit, block or prevent rotation of the chamber body 18 and thus the chamber 12. As shown in FIG. 5, a pin 290 has an elongated cylindrical body 292 with a tapered end 294 and a transverse opening 296 adjacent an end 298 opposite the tapered end 294. A spring-loaded ball 300 is received in a recess adjacent the tapered end 294 and a ring or a cross member 302 is received in the opening 296 adjacent the opposite end 298. The body 292 of the pin 290 is dimensioned to fit into a passage or hole 304 formed in and extending through one projection 146 of the first chamber support portion 144 of the first bracket 130. The body 292 is also dimensioned to fit into each of the two passages 106 in the first disc portion 62 that do not receive a threaded fastener 109.

Advancing the pin 290 through the hole 304 in the first bracket 130 toward the chamber body 18 and the first disc 60 and into a passage 106 in the first disc portion 62 will cause the pin to hold the chamber body and thus the chamber 12 against rotation. The spring-loaded ball 300 will help hold the pin 290 in engagement with the first disc 60. There are two passages 106 in the first disc portion 62 that do not receive a threaded fastener 109, and there are two passages 116 in the second disc portion 64 that do not receive a threaded fastener 119. One such passage 106 in the first disc portion 62 (in the upper right-hand area of the first disc portion 62) and one such passage 116 in the second disc portion 64 (in the lower left-hand area of the second disc portion 64) are disposed approximately 180° apart from one another. By advancing the pin 290 into one of these two passages 106, 116, the chamber body 18 and thus the chamber 12 may be held or locked in position against rotation in a first orientation and a different second orientation disposed approximately 180° apart from one another. If desired, the pin 290 may be employed to engage the second disc 160 though a hole (not shown) in the second bracket 170 or a second pin (not shown) may be similarly employed to engage the second disc 160 though such a hole in the second bracket 170.

When a surgeon or other healthcare provider is to perform a transplantation procedure, the surgeon or other healthcare provider may employ a device such as the device 10 of FIGS. 1-6 in implementing a process or method for performing a medical or surgical procedure on an organ or tissue ex vivo. For example, if the surgeon or other healthcare provider is performing a transplantation of an organ 270, such as a liver, the surgeon or other healthcare provider may position the chamber 12 such that the chamber body 18, including the first chamber component 22, is carried by the support structure 14, in a first orientation, as shown in FIG. 6. In the first orientation, the first chamber component 22 is oriented to provide support for the first surface 275 of the organ 270, when disposed in the chamber body 18. In particular, the upper edge 46 of the rim 26 of the first chamber component 22 is substantially horizontal and the remainder of the first chamber component, including the four angled side members 32a, 32b, 32c, and 32d and the base member 34, is disposed below the rim 26.

The organ 270 is disposed in the chamber body 18 so that the first surface 275 of the ex vivo organ 270 is supported by the first chamber component 22 and the second surface 276 of the organ 270 is exposed to manipulation from outside the chamber body. The first chamber component 22 may directly support the first surface 275 of the organ 270 by being in direct contact with the first surface of the organ or the first chamber component 22 may indirectly support the first surface of the organ by having the first compliant member 272 disposed between the first chamber component and the organ. Depending on the circumstances, the organ 270, such as a liver, may be disposed in the chamber body 18 prior to positioning the chamber body in the first orientation. The second surface 276 of the ex vivo organ 270 or tissue may be exposed to manipulation from outside the chamber body 18 by either removing the second chamber component 24 from the chamber body, if the organ is already disposed in the chamber body before the surgeon or other healthcare provider initiates this method, or by not placing the second chamber component in contact with the first chamber component 22, if the organ 270 is positioned in the chamber body after the chamber body is placed in its first orientation. The organ 270 may be connected to the second and fourth lengths of tubing 282 and 286 so that perfusion liquid or other liquid is delivered to the organ during the medical or surgical procedure.

With the chamber body 18 in its first orientation, the surgeon or other healthcare provider may perform a first medical or surgical procedure on the organ 270. This first medical or surgical procedure, which may, for example, involve removing excess, unwanted, or non-viable tissue from the organ 270 or separating the organ into two viable pieces, if the organ is a liver, for example, is performed by having medical or surgical instruments directed from outside the chamber body 18 manipulate, engage or interact with the organ 270, particularly the second surface 276 of the organ. The surgeon or other healthcare provider may manipulate, engage or interact with the organ 270 by reaching into or otherwise accessing the volume or space that would otherwise be blocked from such access by the second chamber component 24. The manipulation may involve use of, for example, a scalpel or a suturing needle. While the surgeon or other healthcare provider is performing the first medical or surgical procedure, the chamber body 18 and thus the chamber 12 may locked or blocked from or held against rotation by the engagement of the pin 290 with the first disc 60 or by another suitable mechanism.

After performing the first medical or surgical procedure, the surgeon or other healthcare provider may then engage the second chamber component 24 with the first chamber component 22, which in the absence of the second chamber component constitutes, in effect, the chamber body 18. Before the surgeon or other healthcare provider engages the second chamber component 24 with the first chamber component 22, the surgeon or other healthcare provider may place the second compliant member 274 in contact with the second surface 276 of the organ 270 so that the second compliant member 274 is interposed between the second surface of the organ and the second chamber component 24. Thereafter, the surgeon or other healthcare provider may slide the pin 290 out of engagement with the first disc 60 and then rotate the chamber body 18, including the first and second chamber components 22 and 24, around the axis 180 from its first orientation to a second orientation. Rotation of the chamber body 18 may be accomplished by grasping the chamber body and rotating the chamber body by hand or the rotation may be accomplished by operating a motor (not shown) or crank (not shown) coupled to the first or second disc 60 or 160 and thus to the chamber body.

The second orientation of the chamber body 18 is about 180° around the axis 180 from the first orientation. In the second orientation of the chamber body 18, the second chamber component 24 is oriented to provide support for the second surface 276 of the organ 270, when disposed in the chamber body 18. In particular, the lower edge 48 of the rim 26 of the second chamber component 24 becomes the uppermost surface of the second chamber component and is substantially horizontal. The remainder of the second chamber component 24, including the four angled side members 42a, 42b, 42c, and 42d and the base member 44, is disposed below the edge 48 of the rim 36. The organ 270 is disposed in the chamber body 18 so that the second surface 276 of the ex vivo organ 270 is supported by the second chamber component 24 and the first surface 275 of the organ 270 may be exposed to manipulation from outside the chamber body. The second chamber component 24 may directly support the second surface 276 of the organ 270 by being in direct contact with the second surface of the organ or the second chamber component 24 may indirectly support the second surface of the organ by having the second compliant member 274 disposed between the second chamber component and the organ.

When the chamber body 18 has been rotated to its second position, the pin 290 may be engaged with the second disc portion 64 of the first disc 60 to block or prevent rotation of the chamber body 18. The surgeon or other healthcare provider may then remove the first chamber component 22 from engagement with the second chamber component 24, and thus the chamber body 18, and also remove the first compliant member 272 from engagement with the first surface 275 of the organ 270. As a result, the second surface 276 of the ex vivo organ 270 is supported by the second chamber component 24 and the first surface 275 of the organ 270 is exposed to manipulation from outside the chamber body. With the chamber body 18 in its second orientation, the surgeon or other healthcare provider may perform a second medical or surgical procedure on the organ 270. This second medical or surgical procedure, which may, for example, involve removing excess, unwanted, or non-viable tissue from the organ 270 or separating the organ into two viable pieces, if the organ is a liver, for example, is performed by having medical or surgical instruments directed from outside the chamber body 18 manipulate, engage or interact with the organ 270, particularly the first surface 275 of the organ. The surgeon or other healthcare provider may manipulate, engage or interact with the organ 270 by reaching into or otherwise accessing the volume or space that would otherwise be blocked from such access by the first chamber component 22. The manipulation may involve use of, for example, a scalpel or a suturing needle.

If the surgeon or other healthcare provider decides that additional medical or surgical procedures are desirable or necessary and should be performed on the second surface 276 of the organ 270, the surgeon or other healthcare provider may again place first compliant member 272 on the organ and place the first chamber component 22 in a mating orientation in direct contact with the second chamber component 24 so that the chamber body 18 is again complete and can be rotated into its first orientation, as described above. Thereafter, the pin 290 may be engaged to block or prevent rotation of the chamber body 18, the second chamber component 24 may be removed from direct contact with the first chamber component 22, and the second compliant member 274 may be removed from contact with the second surface 276 of the organ 270. The second surface 276 of the organ 270 will then again be exposed to manipulation from outside the chamber 12. The foregoing steps of rotating the chamber body 18 and removing either the first chamber component 22 or the second chamber component 24 and the associated first or second compliant member 272 or 274 may be repeated as required until the organ 270 is ready to be transplanted into a recipient patient's body.

During the performance or implementation of the process or method described above, once the first or chamber-mounted engagement feature 20 is engaged with the second or support-mounted engagement feature 150, at least a portion of the chamber-mounted engagement feature remains engaged with the support-mounted engagement feature even as the first and second chamber components 22 and 24 are individually moved into and out of engagement with one another. Stated differently, the second chamber component 24 can be removed from engagement with the first chamber component 22, and thus the chamber body 18, without disengaging the chamber-mounted and support-mounted engagement features 20 and 150, respectively, from one another when the organ 270 is disposed in the chamber body and the chamber 12 is in the first orientation. Specifically, while the second chamber component 24 is disengaged from the first chamber component 22 and the second disc portions 64 and 164 are disengaged from the first disc portions 62 and 162, the first disc portions 62 and 162 and thus the first and second discs 60 and 160 and the chamber-mounted engagement feature 20 remain engaged with the first and second chamber support portions 144 and 176 of the first and second brackets 130 and 170, respectively, and thus the support-mounted engagement feature 150. Likewise, the first chamber component 22 can be removed from engagement with the second chamber component 24, and thus the chamber body 18, without disengaging the chamber-mounted and support-mounted engagement features 20 and 150, respectively, from one another when the organ 270 is disposed in the chamber body and the chamber 12 is in the second orientation. Specifically, while the first chamber component 22 is disengaged from the second chamber component 24 and the first disc portions 62 and 162 are disengaged from the second disc portions 64 and 164, the second disc portions 64 and 164 and thus the first and second discs 60 and 160 and the chamber-mounted engagement feature 20 remain engaged with the first and second chamber support portions 144 and 176 of the first and second brackets 130 and 170, respectively, and thus the support-mounted engagement feature 150.

Although each of the first and second chamber components 22 and 24 is described and illustrated as generally resembling a frustum of a pyramid with a rectangular base, which permits the chamber body 18 to fit into and rotate within the basin 16, the first and second chamber components may have other shapes. Each of the first and second chamber components 22 and 24 may, for example, be shaped generally as a frustum of a pyramid with a square, rather than a rectangular, base. Each of the first and second chamber components 22 and 24 may alternatively be shaped as hemispheres, as halves of an ellipsoid, halves of a cylinder, or any other geometric shape that would permit the first and second chamber components to be readily engaged and disengaged with one another. The shapes used for the first and second chamber components 22 and 24 and the shape of the basin 16 would be selected to permit the chamber body 18 to fit into and rotate within the basin.

Similarly, while the chamber body 18 is described and illustrated as being comprised of two substantially identical halves or components, other configurations of the chamber body are possible. For example, the rims 26 and 36 of the first and second chamber components 22 and 24 may alternatively be formed as a single member, which may be permanently attached directly to or connected directly to the first and second discs 60 and 160. The removable first chamber component 22 would then comprise the four angled side members 32a, 32b, 32c, and 32d and the base member 34, and the removable second chamber component 24 would then comprise the four angled side members 42a, 42b, 42c, and 42d and the base member 44. Such an alternative chamber body 18 would then have releasable attachment mechanisms, such as latches, to connect each of the alternative first and second chamber components 22 and 24 to the single member comprised of the two rims 26 and 36.

Yet another alternative configuration of the chamber body 18 may be the use of more than two removable chamber components. For example, as described above, the chamber body 18 may comprise a frame, such as a single member formed from the two rims 26 and 36, to which removable chamber components, such as the previously described alternative first and second chamber components 22 and 24, are releasably attached or connected. If the chamber body 18 alternatively comprised three removable chamber components, the frame may alternatively comprise three rims permanently secured to two spaced apart triangular plates to which the first and second discs 60 and 160 may be directly and permanently attached. Any number of removable chamber components may be possible, but as the number of removable chamber components increases, the overall dimensions of the chamber will tend to increase and the amount of working room provided by removing an individual chamber component will tend to decrease. Conversely, the use of two chamber components 22 and 24 that directly engage one another will tend to provide the both the smallest overall dimensions for the chamber 12 and the greatest working room when one of the chamber components is removed.

The device 10 has been described and illustrated as including one mechanism, which includes the pin 290, to limit, block or prevent rotation of the chamber body 18 and thus the chamber 12. As previously indicated, the particular mechanism described and illustrated is just one example of such a mechanism. Other mechanisms may be used, as desired, to facilitate use of the device 10. For example, in one such alternative mechanism, the larger circumference portion of one or both of the first and second discs 60 and 160 may include two notches or indentations located about 180° apart. In lieu of the pin 290, a spring-biased latch member or follower may engage and travel on the larger circumference portion of one or both of the first and second discs 60 and 160. As the follower reaches each notch or indentation, the spring bias will tend to cause the follower to engage and remain in the notch or indentation. By appropriately locating the notches or indentations, the engagement of the follower with one notch on the first or second disc 60 or 160 would tend to maintain the chamber body 18 in the first orientation, while engagement of the follower with the other notch on the first or second disc would tend to maintain the chamber body 18 in the second orientation. As another alternative mechanism, if rotation of the chamber body 18 is accomplished by operating a motor or crank coupled to the first or second disc 60 or 160 and thus to the chamber body 18, the gear train from the motor or crank to the first or second disc may be lockable in positions corresponding the first and second orientations of the chamber body.

More generally, the device 10 has been described and illustrated as a device for use during the final stage of a transplantation process when an ex vivo organ or tissue is about to be implanted into a recipient patient. The device 10 could, however, be used earlier in the transplantation process, such as when an organ or tissue is being removed from a donor's body and/or during transportation of a donated organ or tissue ex vivo. Such use may involve an external, portable source of perfusion fluid, including a pump and a source of electrical power. Such use may also or alternatively involve a portable electric motor and a releasable drive mechanism to connect the motor to one or both of the first and second discs 60 and 160 to enable the chamber body 18 to be rotated periodically or intermittently during transportation of the organ or tissue ex vivo and thereby assist in reducing trauma or damage to the organ or tissue resulting from resting on single surface of the organ or tissue for an extended period during transportation. For example, such a drive mechanism may include a hollow shaft extending from outside the basin through the rim 182 into engagement with one of the first and second discs 60 and 160, thereby providing both a mechanism for delivering rotational movement to the chamber 12 and, via the hollow interior of the shaft, a flow conduit for perfusion liquid. Use of the device 10 earlier in the transplantation process may further or alternatively involve sensors placed on, in, or near the organ or tissue ex vivo and a visually perceptible device, such as a display screen of a hand-held or other device, for monitoring data from such sensors and/or wireless transmission devices to transmit data from such sensors to a remote device, such as a hand-held device, for monitoring such data.

From the above description of the invention, those skilled in the art will perceive improvements, changes and modifications. Such improvements, changes, and/or modifications within the skill of the art are intended to be covered by the appended claims.

Having described the invention, the following is claimed:

1. A method for performing a surgical procedure using a device comprising a chamber including a chamber body configured and dimensioned to extend around an organ or tissue ex vivo, the chamber body including a first removable chamber component and a second removable chamber component, the chamber body being carried by a support structure of the device for rotation about an axis extending through the chamber from a first side of the chamber to an opposite second side of the chamber, the method comprising the steps of:
   (a) positioning the chamber body including the first removable chamber component such that the support structure carries the chamber body and the chamber body is in a first orientation;
   (b) disposing an ex vivo organ or tissue in the chamber body so that a first surface of the ex vivo organ or tissue is supported by the first removable chamber component and a second surface of the ex vivo organ or tissue is exposed to manipulation from outside the chamber body;
   (c) performing a first surgical procedure on the ex vivo organ or tissue;
   (d) engaging the second removable chamber component with the chamber body;
   (e) rotating the chamber body including the first and second removable chamber components around the axis from the first orientation to a second orientation;
   (f) removing the first removable chamber component from engagement with the chamber body so that the second surface of the ex vivo organ or tissue is supported by the second removable chamber component and the first surface of the ex vivo organ or tissue is exposed to manipulation from outside the chamber body; and
   (g) performing a second surgical procedure on the ex vivo organ or tissue.

2. The method of claim 1, wherein the chamber includes a first engagement feature, the support structure including a second engagement feature configured and dimensioned to engage the first engagement feature such that the chamber body is carried by the support structure for rotation about the axis.

3. The method of claim 2, wherein the second removable chamber component is removable from engagement with the chamber body without disengaging the first and second engagement features from one another when the organ or tissue is disposed in the chamber body and the chamber body is in the first orientation so that the first removable chamber component provides support for the first surface of the organ or tissue while the second surface of the organ or tissue is exposed to manipulation from outside the chamber body.

4. The method of claim 2, wherein the first removable chamber component is removable from engagement with the chamber body without disengaging the first and second engagement features from one another when the organ or tissue is disposed in the chamber body and the chamber body is in the second orientation so that the second removable chamber component provides support for the second surface of the organ or tissue while the first surface of the organ or tissue is exposed to manipulation from outside the chamber body.

5. The method of claim 2, wherein the first engagement feature includes a circular member attached to the chamber body, the second engagement feature including a curved surface configured and dimensioned to receive the circular member of the first engagement feature.

6. The method of claim 5, wherein the first engagement feature includes (a) a first circular member directly attached to a first side of the chamber body and (b) a second circular member directly attached to a second side of the chamber body opposite and spaced apart from the first side, the second engagement feature including a first curved surface configured and dimensioned to receive the first circular member of the first engagement feature and a second curved surface configured and dimensioned to receive the second circular member of the first engagement feature, the second curved surface being spaced apart from the first curved surface.

7. The method of claim 2, wherein the first engagement feature includes a disc separable into a first disc portion and a second disc portion, the first disc portion being directly attached to the first removable chamber component and the second disc portion being directly attached to the second removable chamber component.

8. The method of claim 7, wherein the support structure includes a bracket, the second engagement feature including a curved surface portion of the bracket, the curved surface portion being configured and dimensioned to receive the disc of the first engagement feature.

9. The method of claim 2, wherein at least one of the first engagement feature and the second engagement feature is configured and dimensioned to provide a passage along the axis through which fluid may pass from outside the chamber body to inside the chamber body.

10. The method of claim 1, wherein the first removable chamber component and the second removable chamber component when both engaged with the chamber body are disposed opposite one another, the chamber body when carried by the support structure being rotatable around the axis from the first orientation through about 180° to the second orientation.

11. The method of claim 1, wherein the first removable chamber component and the second removable chamber component are configured and dimensioned to engage one another directly to form the chamber body.

12. The method of claim 1, wherein the first removable chamber component is a first half of the chamber body and the second removable chamber component is a second half of the chamber body, the first half of the chamber body being substantially identical in configuration and dimensions to the second half of the chamber body.

13. The method of claim 1, wherein the first removable chamber component includes at least one first drainage opening through which fluid can pass from inside the chamber body to outside the chamber body, the second removable chamber component including at least one second drainage opening through which fluid can pass from inside the chamber body to outside the chamber body.

14. The method of claim 13, further comprising a basin on which the support structure is removably mountable, the basin being positioned to receive fluid from at least one of the at least one first drainage opening and the at least one second drainage opening.

15. The method of claim 14, wherein the chamber includes a first engagement feature, the support structure including a second engagement feature configured and dimensioned to engage the first engagement feature such that the chamber body is carried by the support structure for rotation about the axis, and
wherein the support structure includes a bracket removably mounted on the basin, the second engagement feature including a curved surface portion of the bracket, the curved surface portion being configured and dimensioned to receive a disc portion of the first engagement feature.

16. The method of claim 14, wherein the basin includes at least one passage through which fluid can pass from inside the basin to outside the basin.

17. The method of claim 14, further comprising a cover removably mountable on the basin.

18. The method of claim 14, wherein the basin is configured and dimensioned to permit the chamber to be rotated in the basin when the support structure is mounted on the basin and the chamber body is carried by the support structure.

19. The method of claim 1, further comprising a first cushion member and a second cushion member, the first cushion member being configured and dimensioned to be positioned on the first removable chamber component between the first removable chamber component and the ex vivo organ or tissue, the second cushion member being configured and dimensioned to be positioned on the second removable chamber component between the second removable chamber component and the ex vivo organ or tissue.

20. The method of claim 1, further comprising a mechanism engageable to block rotation of the chamber body about the axis when the chamber body is in one of the first orientation and the second orientation.

* * * * *